(12) United States Patent
Yasunaga et al.

(10) Patent No.: US 7,177,387 B2
(45) Date of Patent: Feb. 13, 2007

(54) SELF-ALIGNING SCINTILLATOR-COLLIMATOR ASSEMBLY

(75) Inventors: Takashi Yasunaga, Waukesha, WI (US); Brian Graves, Waukesha, WI (US); Gerhardt E. Schweinert, Cedarburg, WI (US)

(73) Assignee: General Electric Company, Schenectady, NY (US)

( * ) Notice: Subject to any disclaimer, the term of this patent is extended or adjusted under 35 U.S.C. 154(b) by 99 days.

(21) Appl. No.: 10/711,890

(22) Filed: Oct. 12, 2004

(65) Prior Publication Data

US 2005/0117697 A1    Jun. 2, 2005

Related U.S. Application Data

(60) Provisional application No. 60/481,722, filed on Nov. 29, 2003.

(51) Int. Cl.
*H05G 1/64* (2006.01)
*G21K 1/02* (2006.01)

(52) U.S. Cl. .................. 378/19; 378/98.8; 378/147; 378/149; 378/154; 250/370.09

(58) Field of Classification Search ............... 378/19, 378/98.8, 147, 149, 154; 250/370.09
See application file for complete search history.

(56) References Cited

U.S. PATENT DOCUMENTS 5,099,134 A * 3/1992 Hase et al. ............... 250/505.1
5,487,098 A * 1/1996 Dobbs et al. ................ 378/19
5,799,057 A * 8/1998 Hoffman et al. ............ 378/147
5,848,116 A * 12/1998 Sugihara ..................... 378/19
5,955,733 A * 9/1999 Orava et al. ........... 250/370.08
6,396,898 B1 * 5/2002 Saito et al. .................. 378/19
6,587,538 B2   7/2003 Igarashi et al. .............. 378/19
6,687,334 B2 * 2/2004 Galish et al. ............... 378/147
6,917,644 B2 * 7/2005 Cahn et al. ................. 375/142
6,982,423 B2 * 1/2006 Elgali .................... 250/370.11
2002/0064252 A1   5/2002 Igarashi et al.
2004/0120448 A1 * 6/2004 Ratzmann ..................... 378/4
2004/0217291 A1  11/2004 Hoge

FOREIGN PATENT DOCUMENTS

NL        1026089        11/2004

* cited by examiner

*Primary Examiner*—Allen C. Ho
(74) *Attorney, Agent, or Firm*—Ziolkowski Patent Solutions Group, SC; Michael A. Della Penna; Carl B. Horton (57) ABSTRACT

The present invention is directed to scintillator module for a CT detector as well as an apparatus and method of manufacturing the same. The scintillator module is comprised of a scintillator array having a plurality of scintillators aligned in parallel with respect to one another. A collimator assembly includes a comb having a number of teeth and a plurality of collimator plates positioned proximate to the scintillator array. The scintillator array includes at least one indexing pin extending therefrom. The indexing pin engages the comb and is constructed to improve alignment of the scintillator array relative to the collimator plates.

12 Claims, 5 Drawing Sheets

SELF-ALIGNING SCINTILLATOR-COLLIMATOR ASSEMBLY

CROSS-REFERENCE TO RELATED APPLICATION

This application claims the benefit of U.S. provisional application Ser. No. 60/481,722, filed Nov. 29, 2003.

BACKGROUND OF THE INVENTION

The present invention relates generally to diagnostic imaging and, more particularly, to a self-aligning scintillator-collimator assembly and method of manufacturing same.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator having a plurality of collimator plates for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Image quality can be directly associated with the degree of alignment between the components of the detector. "Cross-talk" between detector cells of a CT detector is common and to some degree is affected by the alignment, or lack thereof, of the detector components. In this regard, cross-talk is typically higher when the components of the CT detector are misaligned.

Cross-talk is generally defined as the communication of data between adjacent cells of a CT detector. Generally, cross-talk is sought to be reduced as cross-talk leads to artifact presence in the final reconstructed CT image and contributes to poor spatial resolution. Typically, four different types of cross-talk may result within a single CT detector. Cross-talk can occur as light from one cell is passed to another through a contiguous layer between the photodiode layer and the scintillator. Electrical cross-talk can occur from unwanted communication between photodiodes. Optical cross-talk may occur through the transmission of light through the reflectors that surround the scintillators. X-ray cross-talk may occur due to x-ray scattering between scintillator cells.

In order to reduce cross-talk, the plates or layers of a collimator are aligned with the cells of the scintillator arrays to very tight and exacting tolerances. This alignment of the plurality of cells of the scintillator array and the plates of the collimator can be a time consuming a labor intensive process. Further, the physical placement or alignment of the collimator to the scintillator array is particularly susceptible to misalignment stack-up. That is, one of the scintillator-collimator assemblies, if unaligned, can detrimentally effect the alignment of adjacent assemblies. Simply, if one collimator-scintillator array combination is misaligned, all subsequently positioned collimator-scintillator array combinations will be misaligned absent implementation of corrective measures. Further, such assemblies require adjusting several detectors when only one of the detectors is misaligned.

Therefore, it would be desirable to design a method and apparatus for the alignment of a collimator and a scintillator module to thereby reduce cross-talk and improve spatial resolution of a final reconstructed image.

BRIEF DESCRIPTION OF THE INVENTION

The present invention is directed to a CT detector and method of manufacturing the same that overcomes the aforementioned drawbacks. The CT detector includes a scintillator module having at least one indexing pin. The indexing pin is constructed to engage a recess between a pair of teeth of a comb designed to align collimating elements of a collimator assembly.

Therefore, according to one aspect of the present invention, a CT detector is disclosed which includes a scintillator module having at least one scintillator and at least one indexing pin connected thereto. The at least one scintillator is configured to be impinged with radiographic energy from a radiographic energy source. A collimator assembly includes a plurality of collimator elements and a plurality of teeth configured to define a relative position of the plurality of collimator elements. A portion of the plurality of teeth is configured to engage the at least one indexing pin.

According to another aspect of the present invention, a scintillator-collimator combination is disclosed which includes a plurality of collimator elements configured to collimate x-rays projected thereat and a scintillator module. The scintillator module has a scintillator pack formed of a material configured to illuminate upon reception of x-rays. A comb having a first set and a second set of teeth is constructed to align the plurality of collimator elements. Additionally, the second set of teeth is constructed to engage the scintillator module and align the scintillator module relative to the plurality of collimator elements. The first set of teeth extends in a direction generally transverse to the second set of teeth. Such a construction forms a collimator assembly and scintillator module that can be quickly and repeat-ably associated.

In accordance with another aspect of the present invention, a CT system is disclosed that includes a rotatable gantry having a bore centrally disposed therein. A table is configured to position a subject for CT data acquisition and is movable fore and aft through the bore. A high frequency electromagnetic energy projection source is positioned within the rotatable gantry and configured to project high frequency electromagnetic energy toward the subject. A detector array is disposed within the rotatable gantry and configured to detect high frequency electromagnetic energy projected by the projection source and impinged by the subject. The detector array includes a plurality of scintillator modules and a collimator assembly. Each scintillator module has a scintillator array and an indexing pin, and the collimator assembly has a plurality of collimator plates. The detector array also includes a detector support having at least one comb of alignment teeth. The alignment teeth are constructed to align the plurality of collimator plates and are constructed to engage an indexing pin to align a scintillator array with a plurality of collimator plates. Such a construction forms a detector array wherein the teeth of the comb align the scintillator module and the collimator, and position the plates relative thereto.

According to yet another aspect of the present invention, a method of manufacturing a CT detector is disclosed which includes providing a scintillator array having at least one locator extending beyond the scintillator array, providing a comb having a plurality of teeth constructed to define a spacing between collimating elements of a collimator, and positioning the at least one locator between at least two of the plurality of teeth.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
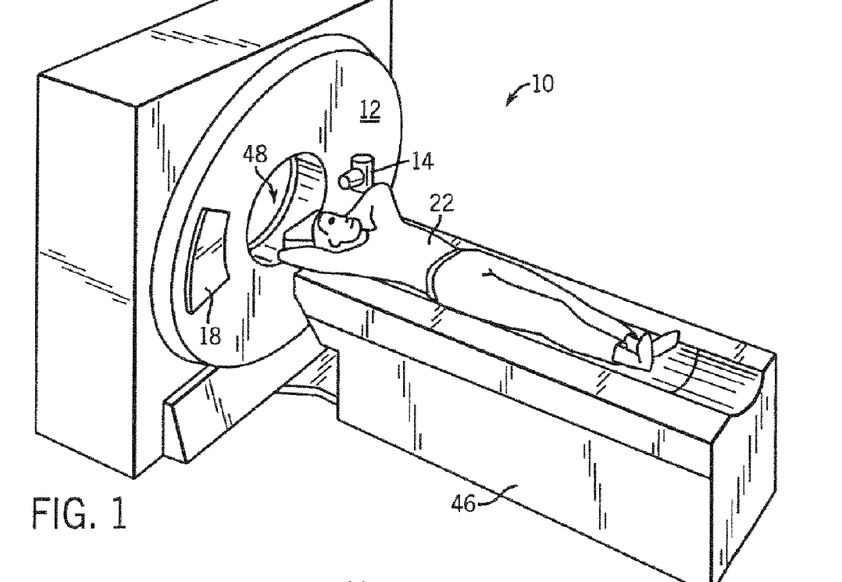
FIG. 1 is a pictorial view of a CT imaging system according to the present invention.
Figure 2:
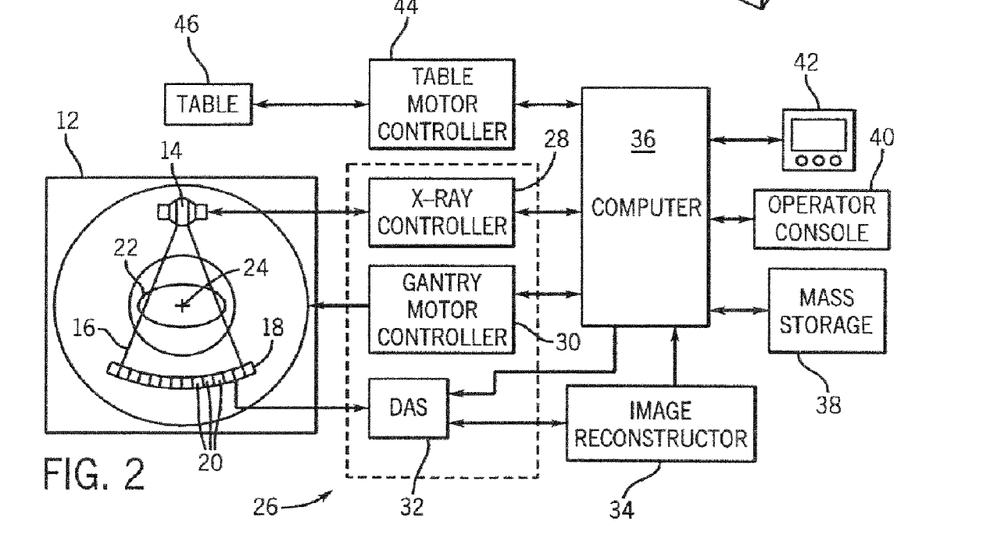
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
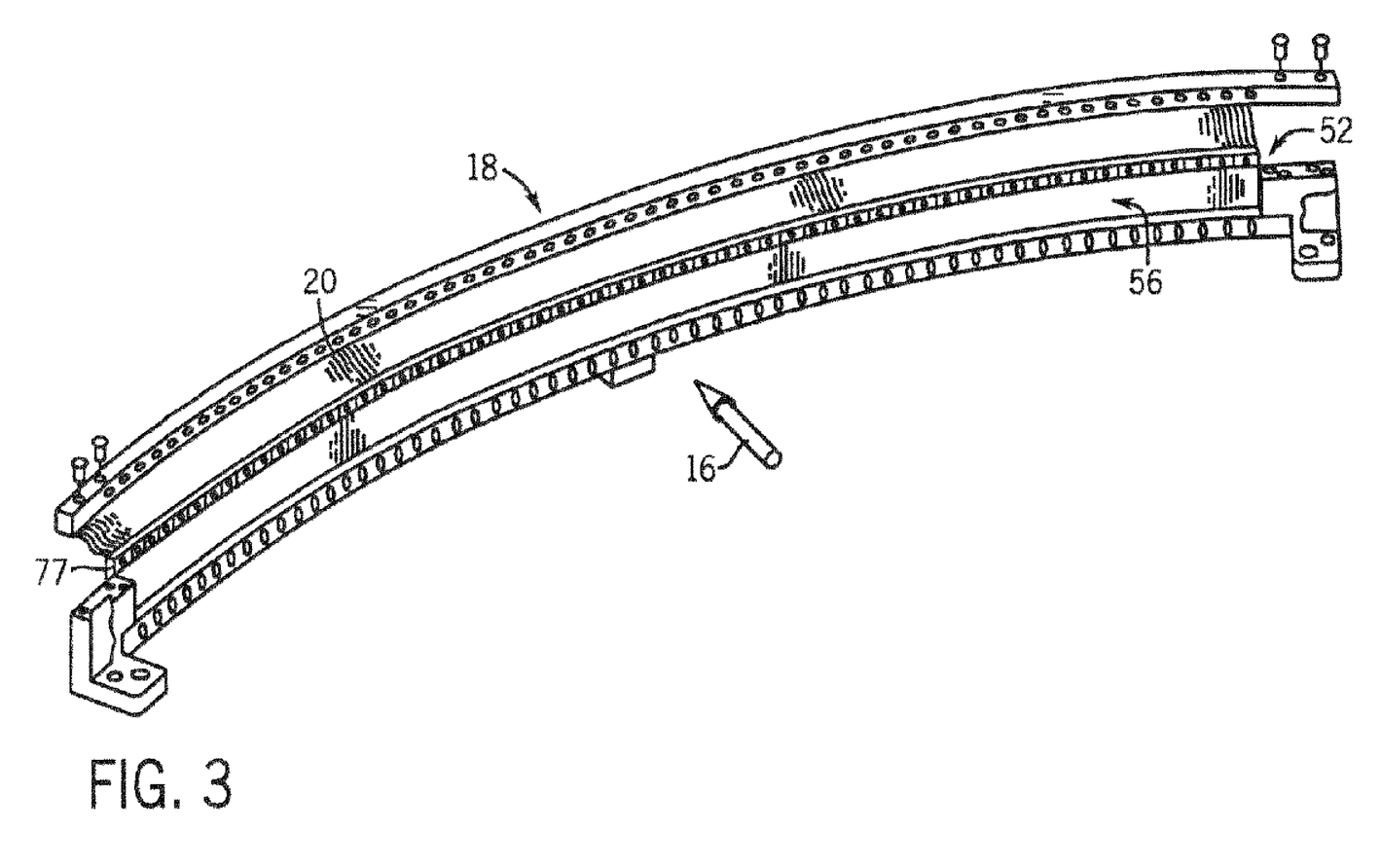
FIG. 3 is a perspective view of one embodiment of a CT system detector array.
Figure 4:
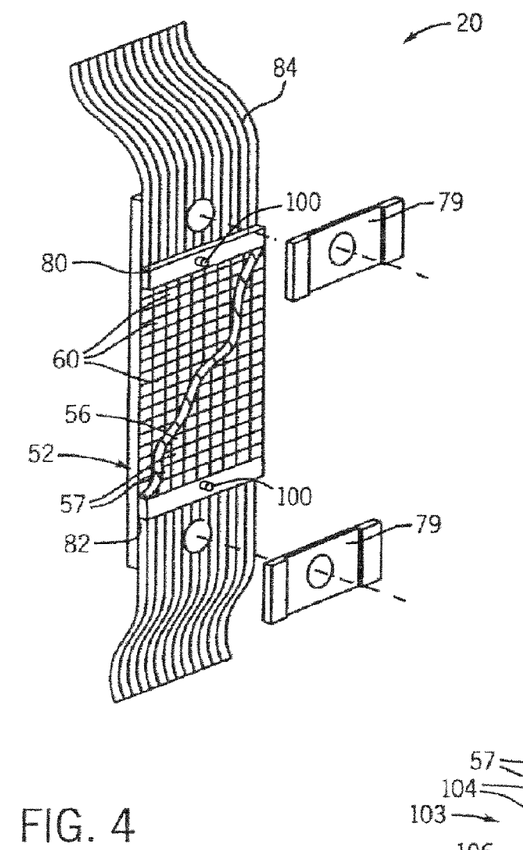
FIG. 4 is a perspective view of one embodiment of a detector of the detector array shown in FIG. 3.

As shown in FIGS. 3 and 4, detector array 18 includes a plurality of single scintillator fibers 57 forming a scintillator array 56. In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, as shown in FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a thin reflector layer (not shown) may be interposed between each scintillator fiber 57 to reduce light scattering from adjacent scintillators. Each detector 20 is secured to a detector frame 77, FIG. 3, by mounting brackets 79.

Referring to FIG. 4, switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
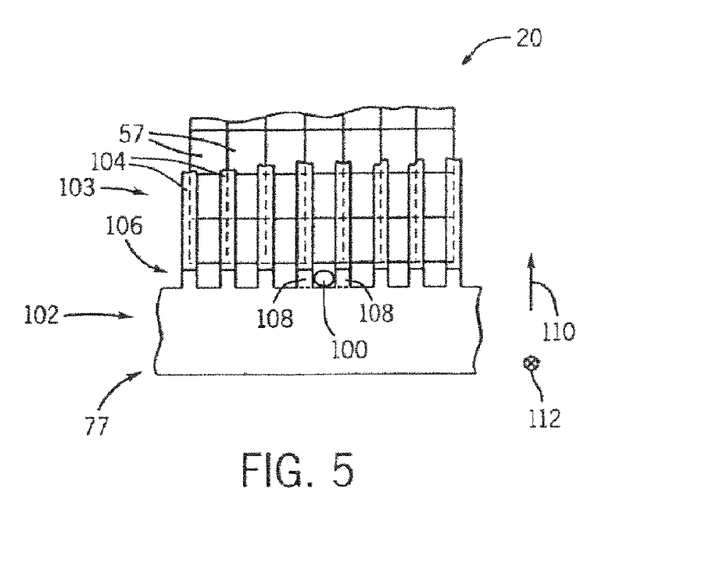
FIG. 5 is a top view of the detector relative to a collimator assembly and detector frame according to the present invention.

Referring to FIG. 5, each detector module 20 is constructed to have a pair of indexing pins 100 that engages a comb 102 integrally formed with or connected to detector frame 77. Comb 102 includes a first set of teeth 106 and a second set of teeth 108. X-rays 16 pass through the plates 104 of collimator assembly 103 and impinge upon scintillators 57. It is understood that comb 102 does not extend over the scintillator array 56 of the detector 20. As such, while comb 102 positions collimator 103 relative to the scintillator array 56, comb 102 does not interfere with the passage of x-rays through the collimator 103 to the scintillator array.

First set of teeth 106 of comb 102 extend in a direction, indicated by arrow 110, and second set of teeth 108 of comb 102 extend in another direction, indicated by arrow 112, generally transverse to direction 110. In this regard, the second set of teeth has a height greater than that of the first set of teeth. As such, the second set of teeth defines a recess sized to snuggly receive an indexing pin 100. Moreover, the spacing between the adjacent teeth of the first set of teeth and the second set of teeth is uniform. This opening defines the direction or gap between the collimator plates. That is, when positioning the collimator plate 104, teeth 106, 108 are used to achieve a uniform alignment and spacing. Plates 104 are generally aligned with the scintillators in order to minimize x-ray cross-talk. It is understood that plates 104 could be constructed to substantially match the construction of different scintillator constructions. These constructions include, but are not limited to, scintillators having generally cellular constructions. Moreover, the collimator plates may extend along the x-axis, z-axis, or both. It is noted that the first set of teeth 106, by extending in direction 110, do not obstruct or interfere with the engagement of indexing pin 100 with second set of teeth 108. Collimator 103 is positioned between detector 20 and x-ray source 14 such that plates 104 are aligned with the scintillators 57 of the scintillator array 56. As such, comb 102 not only defines the spacing between adjacent plates 104, but also aligns the collimator and the scintillator. Although shown as a one-dimensional collimator, it is understood that collimator 103 could be constructed to be a two-dimensional collimator and therefore extend across the scintillator module in both the x and z-directions. Also, while only one comb 102 is shown, it is contemplated that a second comb may also be used to align the collimator plate and scintillator array at each respective end thereof. As such, the scintillator pack may include two indexing pins, aligned with one another, but at opposite ends of the module.

Scintillators 57 of scintillator array 56, particularly for multi-slice detectors, are commonly oriented in two orthogonal dimensions, generally the x and the z-directions. In order to minimize x-ray cross-talk between adjacent scintillators 57, the plates 104 of the collimator are aligned with the scintillators of the scintillator array. The plates of the collimator must also be precisely oriented relative to one another to ensure uniform spacing between adjacent plates. The teeth 106,108 of comb 102 define a spacing between collimator plates or elements and therefore ensure a precise orientation of each of the plates of collimator 103 relative to each other, and the precise alignment of collimator 103 and scintillator array 56.

Each scintillator array 56 is also indexed to the position of its respective collimator 103 and associated plates 104. This construction reduces stack-up error between adjacent scintillator/collimator arrays resulting from the misalignment of one scintillator/collimator alignment. As such, any stack-up error associated with adjacent scintillator-collimator pairs is significantly reduced.

Another stack-up error is reduced in the assembly of individual scintillators. The indexing pins are positioned relative to the positioning of the scintillator pixels. By positioning the indexing pins relative to the pixels of the scintillator, any stack-up error associated with the relationship between the indexing pins and the scintillator is reduced. As such, serviceability of a detector according to the present invention is improved as the indexing reference points, i.e. the indexing pins and the teeth of the comb, are integrally formed into the components of the device.

Pins 100 are also formed to index the detector 20 to a rail of detector frame 77 as shown in FIG. 5. Such a construction ensures that a plurality of detectors, when attached to the detector frame, will be aligned therewith prior to connection thereto. Such a construction reduces the time required to associate the individual detectors to the frame during the initial assembly and/or during servicing.

Figure 6:
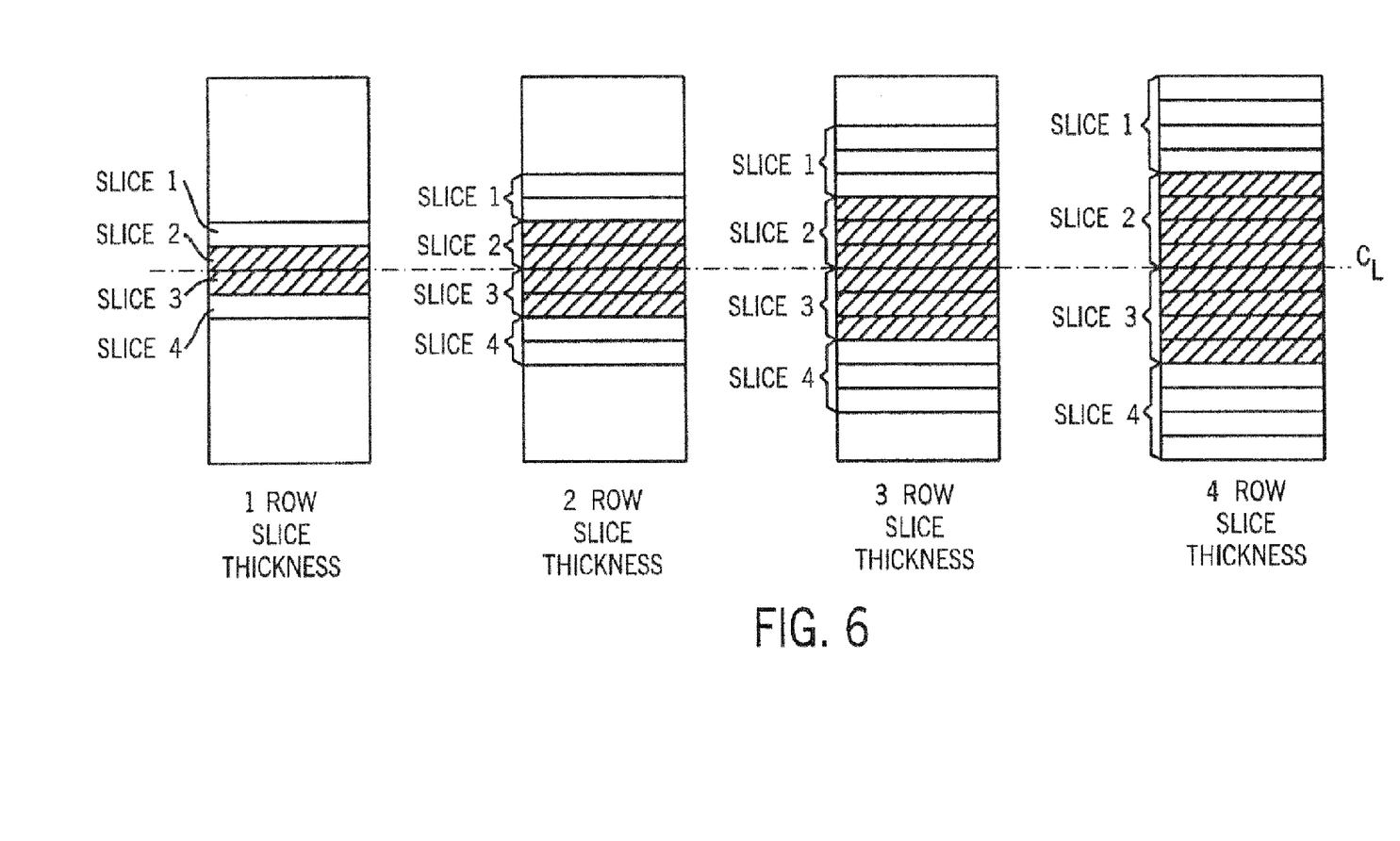
FIG. 6 is illustrative of various configurations of the detector in FIG. 4 in a four-slice mode.

Referring now to FIG. 6, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 7:
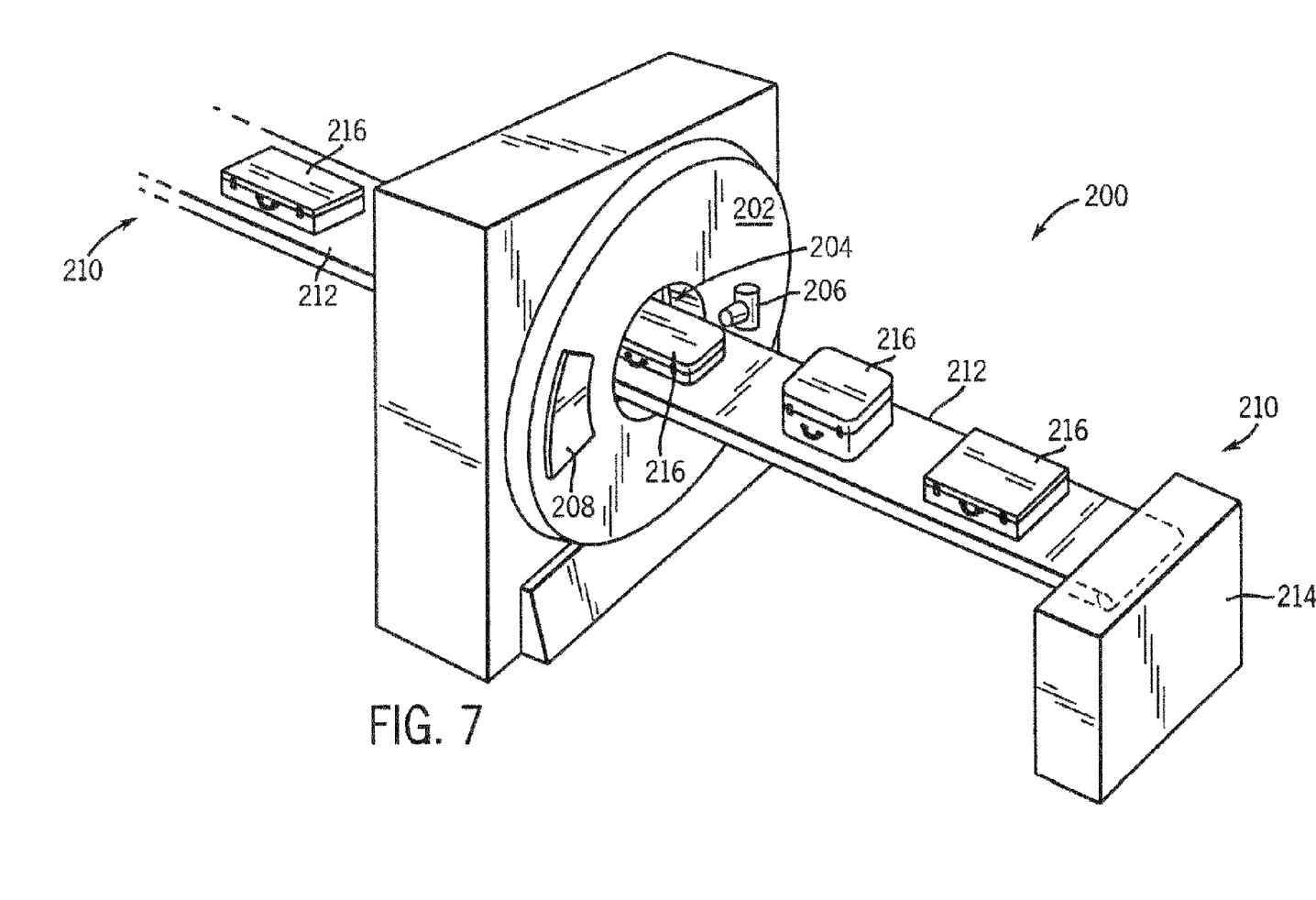
FIG. 7 is a pictorial view of a CT system for use with a non-invasive package inspection system.

Referring now to FIG. 7 package/baggage inspection system 200 includes a rotatable gantry 202 having an opening 204 therein through which packages or pieces of baggage 216 may pass. The rotatable gantry 202 houses a high frequency electromagnetic energy source 206 as well as a detector assembly 208 having scintillator arrays comprised of scintillator cells similar to that shown in FIG. 6. A conveyor system 210 is also provided and includes a conveyor belt 212 supported by structure 214 to automatically and continuously pass packages or baggage pieces through opening to be scanned. Objects are fed through opening by conveyor belt 212, imaging data is then acquired, and the conveyor belt 212 removes the packages 216 from opening 204 in a controlled and continuous manner. As a result, postal inspectors, baggage handlers, and other security personnel may non-invasively inspect the contents of packages 216 for explosives, knives, guns, contraband, etc.

Therefore, according to one embodiment of the present invention, a CT detector includes a scintillator module having at least one scintillator and at least one indexing pin connected thereto. The at least one scintillator is configured to be impinged with radiographic energy from a radiographic energy source. A collimator assembly includes a plurality of collimator elements and a plurality of teeth configured to define a relative position of the plurality of collimator elements. A portion of the plurality of teeth is configured to engage the at least one indexing pin.

According to another embodiment of the present invention, a scintillator-collimator combination includes a plurality of collimator elements configured to collimate x-rays projected thereat and a scintillator module. The scintillator module has a scintillator pack formed of a material configured to illuminate upon reception of x-rays. A comb having a first set and a second set of teeth is constructed to align the plurality of collimator elements and the second set of teeth is constructed to engage the scintillator module and align the scintillator module relative to the plurality of collimator elements. The first set of teeth extends in a direction generally transverse to the second set of teeth.

In accordance with another embodiment of the present invention, a CT system includes a rotatable gantry having a bore centrally disposed therein. A table is configured to position a subject for CT data acquisition and is movable fore and aft through the bore. A high frequency electromagnetic energy projection source is positioned within the rotatable gantry and configured to project high frequency electromagnetic energy toward the subject. A detector array is disposed within the rotatable gantry and configured to detect high frequency electromagnetic energy projected by the projection source and impinged by the subject. The detector array includes a plurality of scintillator modules and a collimator assembly for each scintillator module. Each scintillator module has a scintillator array and an indexing pin and each collimator assembly has a plurality of collimator plates. The detector array also includes a detector support having at least one comb of alignment teeth. The alignment teeth are constructed to align the plurality of collimator plates and is constructed to engage an indexing pin to align a scintillator array with the plurality of collimator plates.

According to yet another embodiment of the present invention, a method of manufacturing a scintillator module is disclosed which includes providing a scintillator array having at least one locator extending beyond the scintillator array, providing a comb having a plurality of teeth constructed to define a spacing between collimating elements of a collimator, and positioning the at least one locator between at least two of the plurality of teeth.

The present invention has been described in terms of the preferred embodiment, and it is recognized that equivalents, alternatives, and modifications, aside from those expressly stated, are possible and within the scope of the appending claims.

What is claimed is:

1. A CT detector comprising:
   a scintillator module including at least one scintillator configured to be impinged with radiographic energy from a radiographic energy source;
   at least one indexing pin connected to the scintillator module; and
   a collimator assembly having a plurality of collimator elements and a plurality of teeth configured to define a relative position of the plurality of collimator elements and a portion of the plurality of teeth configured to engage the at least one indexing pin, and wherein at least two of the plurality of teeth are constructed to flank an indexing pin.

2. The CT detector of claim 1 wherein the at least one scintillator includes a plurality of scintillators uniformly arranged in a scintillator array.

3. The CT detector of claim 1 further comprising at least one photodiode configured to detect illumination of the at least one scintillator.

4. The CT detector of claim 1 incorporated into a rotatable gantry of a CT imaging system.

5. A scintillator-collimator combination comprising:
   a plurality of collimator elements configured to collimate x-rays projected thereat;
   a scintillator module having a scintillator pack formed of a material configured to illuminate upon reception of x-rays;
   a comb having a plurality of teeth constructed to align the plurality of collimator elements and constructed to engage the collimator module and align the scintillator module relative to the plurality of collimator elements; and
   wherein the scintillator module further comprises a locating pin constructed to snuggly engage a recess of the comb, wherein the recess is defined between two of the plurality of teeth.

6. The scintillator-combination of claim 5 wherein the locating pin is configured to align the scintillator pack with respect to the plurality of collimator elements such that the scintillator module does not overlap two collimator elements spaced apart from one another a distance equal to a width of the scintillator module.

7. The scintillator-collimator combination of claim 5 configured to be optically coupled to a photodiode array and configured to detect illumination from the scintillator pack and output electrical signals responsive thereto.

8. The scintillator-collimator combination of claim 5 incorporated into a CT imaging system designed to acquire diagnostic data of a medical patient.

9. A CT system comprising:
   a rotatable gantry having a bore centrally disposed therein;
   a table movable fore and aft through the bore and configured to position a subject for CT data acquisition;
   a high frequency electromagnetic energy projection source positioned within the rotatably gantry and configured to project high frequency electromagnetic energy toward the subject; and
   a detector array disposed within the rotatably gantry and configured to detect high frequency electromagnetic energy projected by the projection source and impinged by the subject, the detector array including:
   a plurality of scintillator modules, each having a scintillator array and an indexing pin;
   a collimator assembly having a plurality of collimator plates; and
   a detector support having at least one comb of alignment teeth, the alignment teeth constructed to align the plurality of collimator plates and engage an indexing pin to align a scintillator array with the plurality of collimator plates.

10. The CT system of claim 9 wherein the alignment teeth define a uniform spacing between collimator plates of the plurality of collimator plates.

11. The CT system of claim 9 wherein the indexing pin laterally extends beyond an end of a respective scintillator array.

12. A method of manufacturing a CT detector comprising the steps of:
   providing a scintillator away having at least one locator extending beyond the scintillator array;
   providing a comb having a plurality of teeth constructed to define a spacing between collimating elements of a collimator; and
   positioning the at least one locator between at least two of the plurality of teeth.

* * * * *

UNITED STATES PATENT AND TRADEMARK OFFICE
CERTIFICATE OF CORRECTION

PATENT NO. : 7,177,387 B2
APPLICATION NO. : 10/711890
DATED : February 13, 2007
INVENTOR(S) : Yasunaga et al.

It is certified that error appears in the above-identified patent and that said Letters Patent is hereby corrected as shown below:

Col. 8, line 57 (Claim 12), delete "away" and substitute therefor --array--.

Signed and Sealed this

Tenth Day of April, 2007

JON W. DUDAS
*Director of the United States Patent and Trademark Office*